United States Patent [19]

Atkinson et al.

[11] Patent Number: 5,261,459
[45] Date of Patent: Nov. 16, 1993

[54] MINIATURE DUCKBILL VALVE HAVING A LOW CRACKING PRESSURE AND HIGH FLOW RATE

[75] Inventors: Gordon E. Atkinson, Cedarville; James R. Kunce, Springfield; James C. Bailey, Yellow Springs, all of Ohio

[73] Assignee: Vernay Laboratories, Inc., Yellow Springs, Ohio

[21] Appl. No.: 986,378

[22] Filed: Dec. 7, 1992

[51] Int. Cl.[5] ............................................. F16K 15/14
[52] U.S. Cl. .................................................... 137/846
[58] Field of Search ......................... 137/846, 847, 850

[56] References Cited

U.S. PATENT DOCUMENTS

| | | | |
|---|---|---|---|
| 3,889,710 | 6/1975 | Brost | 137/512.15 |
| 4,354,492 | 10/1982 | McPhee | 128/214 |
| 4,535,818 | 8/1985 | Duncan et al. | 137/846 |
| 4,535,819 | 8/1985 | Atkinson et al. | 137/846 |
| 4,566,493 | 1/1986 | Edwards et al. | 137/846 |
| 4,612,960 | 9/1986 | Edwards et al. | 137/846 |
| 4,615,693 | 10/1986 | Paradis et al. | 604/122 |
| 5,010,925 | 4/1991 | Atkinson | 137/846 X |

FOREIGN PATENT DOCUMENTS 2094443 9/1982 United Kingdom ................ 137/846

Primary Examiner—Robert G. Nilson
Attorney, Agent, or Firm—Biebel & French

[57] ABSTRACT

A miniature valve is provided for use in a medical administration set wherein the valve is designed to be fit into very small areas while operating with performance characteristics comparable to those provided by larger valves. The valve is formed as a duckbill valve having very thin substantially planar lips extending in converging relationship to each other. A slit is defined by the lips at an outlet end of the valve wherein the slit is movable to an open position as the lips pivot about a pivot point located on the lips in spaced relation to the outlet end. A support structure in the form of a sleeve is provided for ensuring that the contact surfaces remain in alignment with each other during operation of the valve and to prevent the thin, delicate lips from inverting when a large back pressure force is applied and for improving the inherent sealing characteristics of duckbill valves. In addition, a thin area is provided adjacent to the inlet end of the valve for decoupling the lips from forces which are applied to the valve at the inlet end which could tend to bias the lips apart.

20 Claims, 8 Drawing Sheets

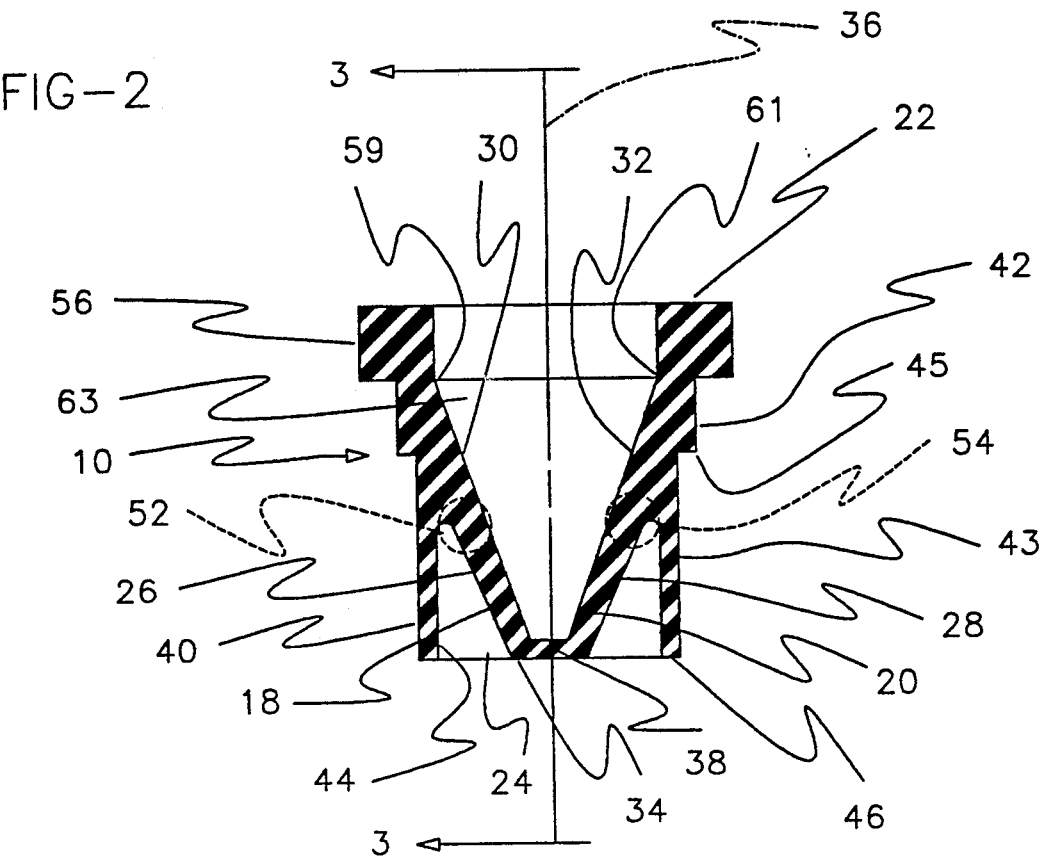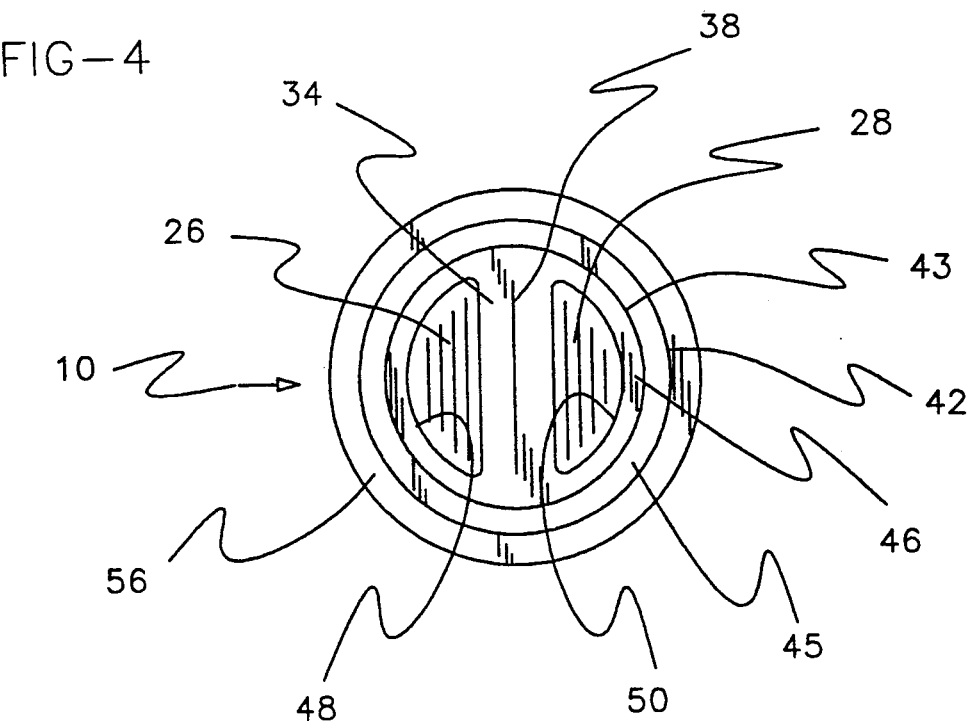

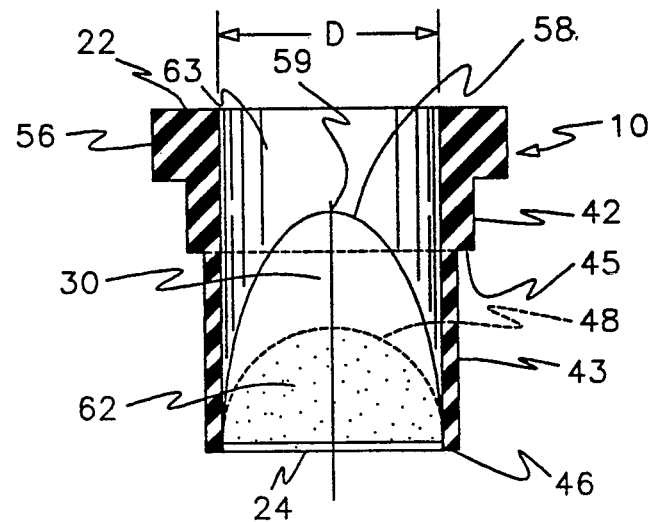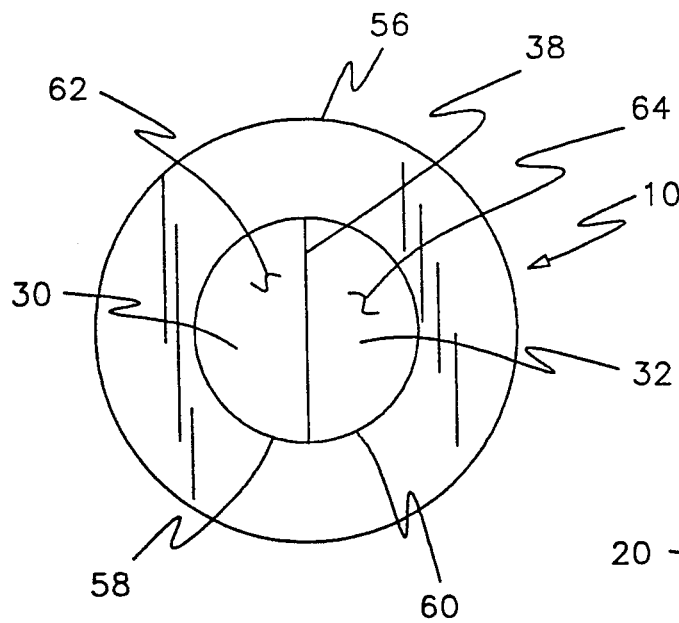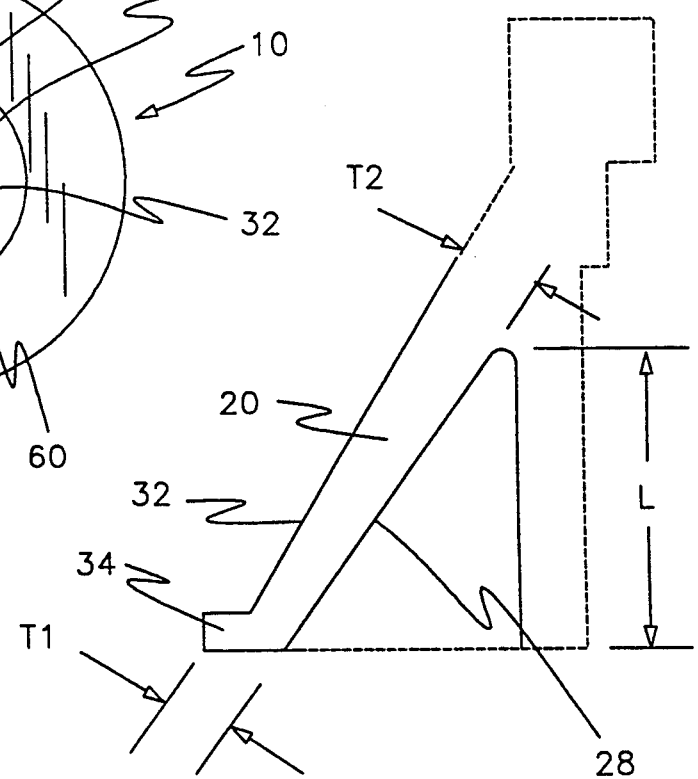

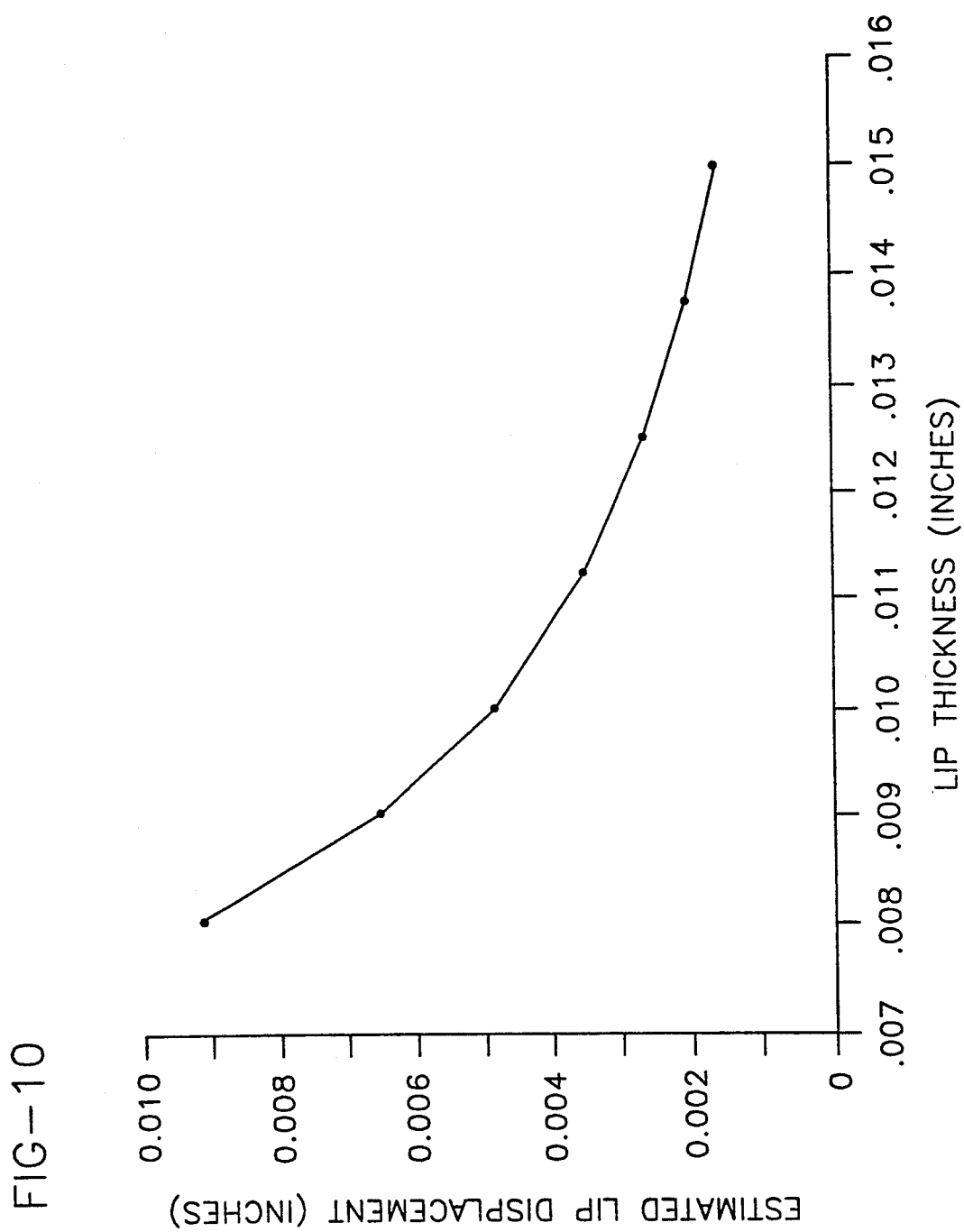

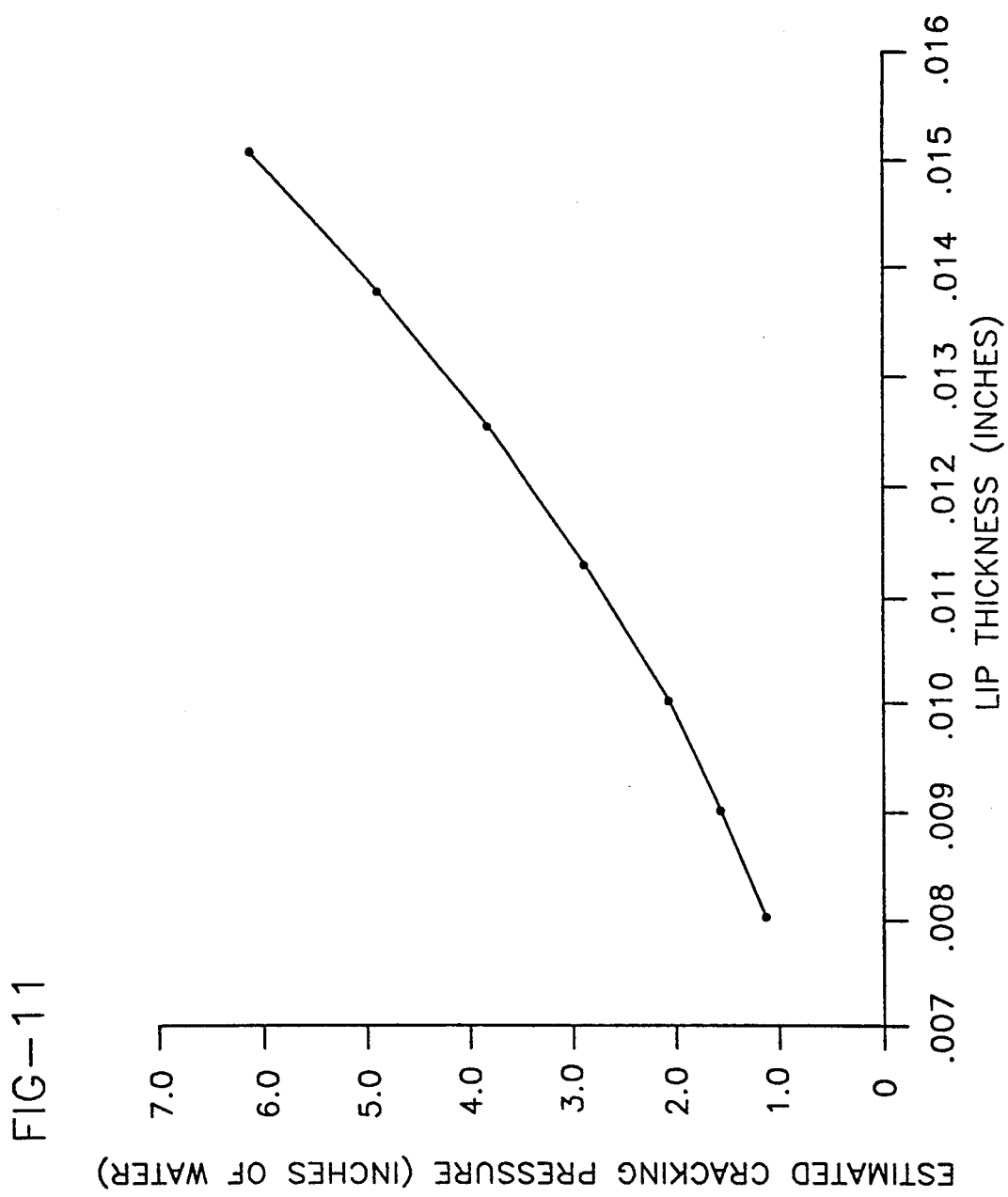

MINIATURE DUCKBILL VALVE HAVING A LOW CRACKING PRESSURE AND HIGH FLOW RATE

BACKGROUND OF THE INVENTION

The present invention relates to a duckbill check valve for use in medical applications, and more particularly, to a miniaturized duckbill flow control valve which operates in forward flow at a low cracking pressure and which provides high volume flow rates.

In a typical administration set arrangement, a Y-site is used to combine two fluid supply lines into a single fluid line leading to an infusion site on a patient. One supply line generally provides a continuous flow of a saline or equivalent fluid and the other supply line is commonly used to provide a prescribed quantity of medication. When the medication is flowing through the Y-site, a check valve provided in the saline line closes in response to fluid pressure exerted by the medication to prevent the medication from flowing into the saline line. A poor check valve seal could permit the medication to enter the saline solution which may result in incomplete delivery of the prescribed quantity of medication.

In addition, check valves for administration sets must also be capable of providing forward fluid flow at very low cracking pressures. This is particularly true when the check valve is provided in the medication supply line. As the medication is administered, the pressure provided by the fluid head continually decreases until a small quantity of the medication is located in the tubing leading to the valve, at which time the pressure head is too low to maintain the valve open, and fluid flow ceases without delivering the entire quantity of medication. Thus, by decreasing the forward flow cracking pressure for the valve, it is possible to ensure that all, or nearly all, of the prescribed medication will be delivered to the patient.

Further, it is important for check valves to introduce as little restriction as possible to the flow of fluid through an administration set. For example, in emergency situations it is desirable for the valve to permit a high flow rate for purging the line of air prior to connecting it to the patient whereby a prescribed medication may be administered without undue delay.

One type of known check valve for use in medical administration sets includes a rubber or elastomeric disk which is located within a rigid housing. The housing typically includes an annular plastic seat for engaging with the disk whereby the disk and seat form a seal preventing back flow through the valve. In order to provide flow through the valve in a forward direction, the elastomeric disk moves in a longitudinal direction out of contact with the seat of the housing whereby fluid may flow around the periphery of the disk as it passes through the valve. Typical disk-type check valves are shown in U.S. Pat. Nos. 3,889,710 to Brost, 4,354,492 to McPhee, and 4,615,693 to Paradis et al.

One limiting characteristic of disk valves results from providing a large sealing area where the rubber disk contacts the hard plastic seat of the housing. As a result of having two dissimilar materials contacting each other across a relatively large area, there is a high probability that leakage will occur due to minute irregularities between the surfaces formed by the elastomeric disk and the plastic housing seat whereby small fissures are formed for permitting fluid leakage during back flow conditions. In addition, disk valves are often subject to variations in performance as a result of changes in the orientation of the valve. For example, in use with a Y-site, the valve may be oriented in an inverted direction and the weight of the disk will be a factor influencing the responsiveness of the valve depending upon the orientation of the valve.

Duckbill valves are another type of valve used in administration sets as a check valve. A duckbill valve is formed of two converging valve lips which meet at a slit wherein the lips are adapted to move apart to open the slit for flow in a forward direction. Usually, the valve is molded unslit and the slit is cut into the valve subsequent to the molding operation such that a pair of complementary mating surfaces are defined on the opposing lips. The valve is preferably formed of a soft elastomeric material such that a positive seal is formed between the lips when the slit is closed to prevent leakage in a back flow direction. In addition, the duckbill valve is adaptable for miniaturization in that the slit provides for a large flow area since the length of the slit when the valve is in the closed position is much less than the circumference of the aperture formed when the slit moves to an open position. Further, because of its inherent stability, the duckbill valve is far less position sensitive than disk valves such that, regardless of the orientation of the valve, the duckbill valve will have consistent performance characteristics.

U.S. Pat. Nos. 4,535,819 to Atkinson et al, 4,535,818 to Duncan et al, 4,566,493 to Edwards et al and 4,612,960 to Edwards et al all disclose duckbill valve structures which are adapted to be used in a medical fluid administration set. In addition, these patents also disclose providing a housing structure wherein the retention of residual air in the area around the valve is minimized by providing a housing structure which extends close to the valve lips whereby problems associated with purging the system of air are minimized. These valves typically require an alignment tab on the valve for cooperating with a slot on the housing whereby the valve is properly aligned with the housing. In addition, these valves are disclosed as being used in conjunction with Y-sites for medical administration sets. However, the size of these valves does not permit them to be directly incorporated into the Y-site, but rather the valve must be enclosed in a housing attached to a branch extending from the Y-site, as shown for example in U.S. Pat. No. 4,535,818.

Accordingly, there is a need for a miniature valve for use in the fluid lines for a medical administration set wherein the valve has a low cracking pressure, accommodates a high fluid flow rate, provides a reliable and positive checking of fluid flow in the reverse flow direction, and which is also relatively insensitive to changes in orientation.

SUMMARY OF THE INVENTION

The present invention provides a miniature duckbill valve for permitting fluid flow in a first direction and for preventing fluid flow in a second opposite direction, the valve comprising a pair of substantially planar lips extending in converging relationship in a direction from an inlet end of the valve to an outlet end of the valve, means defining a slit between the lips at the outlet end, means defining a cylindrical inner wall intersecting the lips along respective intersection lines, the inner wall and the lips defining a longitudinal axis for the valve, means defining a pivot area on each of the lips between the outlet end and the intersection lines, and wherein the lips are formed as extremely thin highly flexible members such that a minimal force for resisting opening of the slit is applied through the lips from the pivot areas to the slit.

In another aspect of the invention, the miniature duckbill valve further includes a cylindrical sleeve extending around the lips and supporting the lips adjacent to opposing ends of the slit at the second end of the valve, and the sleeve is formed with first and second outer diameters, the first outer diameter being larger than the second outer diameter for cooperating with a cylindrical interior wall of a housing for mounting the miniature valve such that the second outer diameter is maintained out of contact with the housing.

In a further aspect of the invention, the sleeve intersects the lips adjacent to the pivot areas for the lips, and a support pivot area is defined between the lip pivot areas and the inlet end of the valve for decoupling the lips from pivotal forces produced at the inlet end.

Thus, it is an object of the present invention to provide a duckbill valve having lips which form a delicate flaccid structure whereby the valve will operate at a low cracking pressure for permitting forward flow through the valve. In addition, the valve is constructed having a maximum diameter for the sleeve of approximately 0.164 inch and with a maximum length of approximately 0.188 inch such that the present valve is constructed as a very small unit which is also capable of accommodating relatively high volume flow rates.

Other objects and advantages of the invention will be apparent from the following description, the accompanying drawings, and the appended claims.

BRIEF DESCRIPTION OF THE DRAWINGS

FIG. 2 is a cross-sectional view taken through the longitudinal center of the valve;

FIG. 3 is a cross-sectional view taken along line 3—3 in FIG. 2;

FIG. 4 is an end view taken from the outlet end of the valve;

FIG. 5 is an end view taken from the inlet end of the valve;

FIG. 6 is a cross-sectional view depicting a cross-sectional area of one lip;

FIG. 10 is a graph plotting the theoretical displacement of the lips in relation to variations in the thickness of the lips; and FIG. 11 is a graph plotting the theoretical cracking pressure in relation to variations in the thickness of the lips.

DETAILED DESCRIPTION OF THE PREFERRED EMBODIMENT

Figure 1:
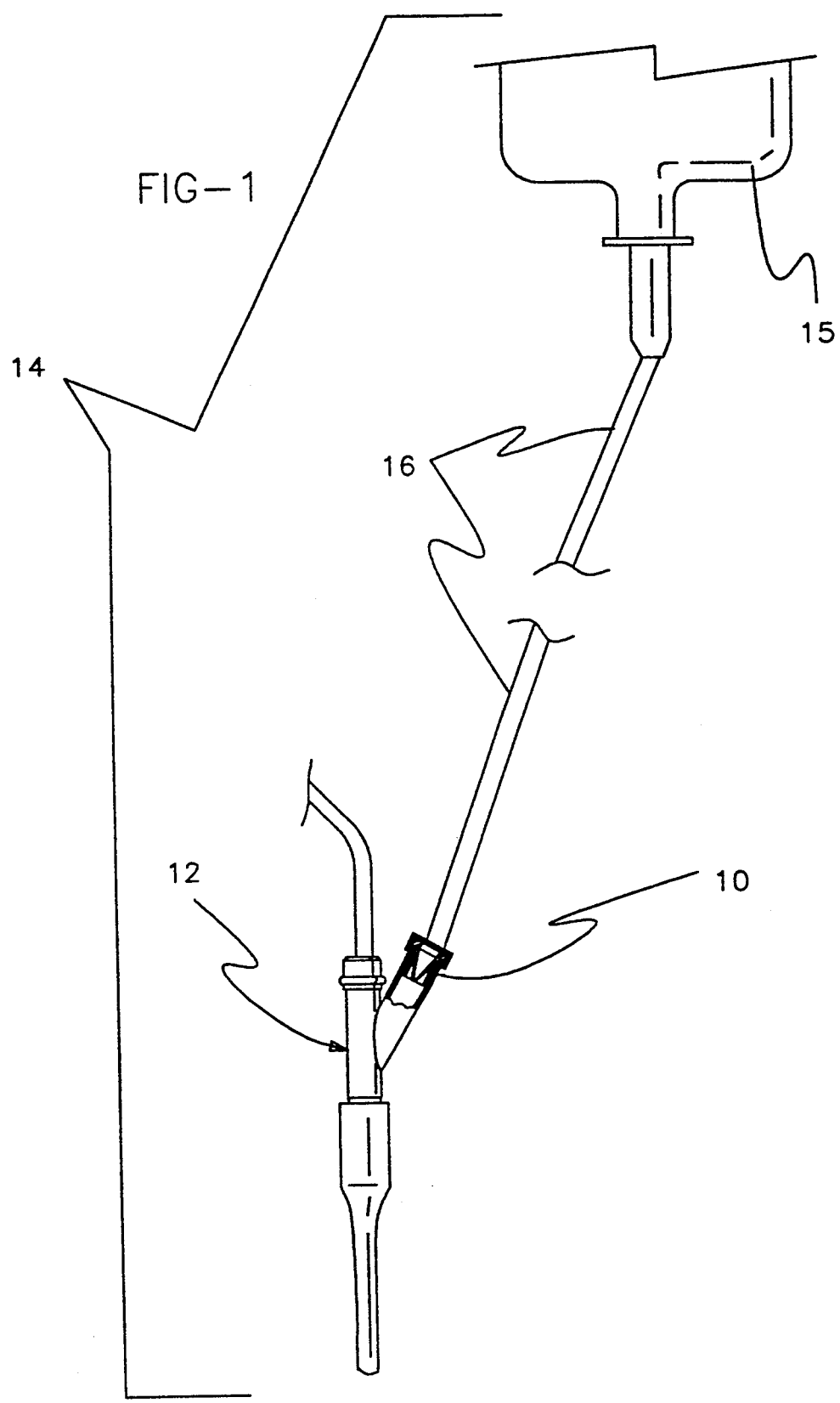
FIG. 1 is a diagrammatic view depicting the valve of the present invention incorporated into a Y-site in a medical administration set.

The present invention provides a miniature duckbill valve 10 which is particularly suited to use within a Y-site 12 or other in-line attachment site for a medical fluid administration set 14, as is shown in FIG. 1. As noted above, one problem associated with prior art duckbill valves is the necessity of providing a separate housing for containing a duckbill valve whereby the valve may be attached to the housing of a Y-site or placed at some other location within a medical administration set. A typical medical fluid administration set commonly includes a medical fluid source 15 and fluid lines or tubing 16 having an inner diameter on the order of 0.1 inch, and it is desirable to have a valve for controlling flow through such lines wherein the size of the valve is of approximately the same order of magnitude as the fluid lines whereby the valve may be incorporated into existing administration set equipment, such as Y-sites, without requiring extensive retooling for the production of the Y-site. In addition, a very small valve provides for a reduction of area for potential entrapment of air which must be purged before fluids may be administered.

It has been found that a simple scaling down of existing valve designs does not provide a valve having satisfactory performance characteristics in that, as a duckbill valve is reduced in size, the relationship between the pressure area, i.e. the area on the inside of the lips of the duckbill valve which is acted on by a fluid pressure to open the valve lips for forward fluid flow, and the stiffness of the lips becomes increasingly critical to the performance of the valve. Specifically, it has been found that with a decrease in the valve size there is a corresponding decrease in the pressure area and an increase in the amount of pressure required to open the valve.

In addition, as the size of the valve is decreased, the characteristics of the material forming the valve also become increasingly critical. For example, silicone elastomers are commonly used in medical applications and, although it is known to form duckbill valves from a silicone material, it has been found that the characteristic of silicone to stick to itself in varying degrees, depending upon the particular type of silicone, becomes increasingly critical as the valve size is decreased wherein increased sticking results in a higher and erratic cracking pressure for opening the valve. At the same time, it is also desirable to provide a highly elastomeric material which will permit the slit between the lips to open a sufficient amount to allow a high fluid flow rate through the valve.

Further, the problems associated with selecting a particular material providing the desired performance characteristics are compounded when the valve is used in a medical application, such as within a medical fluid administration set, in that the material must pass a cytotoxicity test to ensure that the material is not toxic to human tissue cells. Thus, while some forms of silicone comprise a non-toxic, elastic material which is well suited for use in medical valves, its tendency to stick to itself requires that the valve be designed with particular physical characteristics which permit the valve to both open at a specified low cracking pressure and accommodate high flow rates.

Another parameter which has been found critical to miniature valve design is the length of the slit defining the opening between the valve lips wherein the slit length preferably closely corresponds to the interior diameter of the valve. In order to provide a low cracking pressure for opening the valve, it is desirable to provide a long slit, and in a miniature valve a small increase in the length of the slit corresponds to a significant reduction in cracking pressure such that it is desirable to provide as long a slit as possible within the small dimensions of the valve.

In view of the above-described parameters controlling the design of a duckbill valve, it should be noted that as a valve is decreased in size, the size of the pressure area for actuating the slit to open also decreases leading to an increase in cracking pressure. Further, although the lip thickness, and therefore also the stiffness, decreases with decreasing valve size, this decrease in lip thickness is not sufficient to compensate for the increase in cracking pressure resulting from the decreased pressure area. This is because, as the valve size is decreased, the pressure area decreases in a squared relationship as compared to a linear reduction in the valve size and the lip thickness. Further, it has been found that there are practical limits on the extent to which the thickness of the lips may be decreased, as will be discussed further below.

Another consideration in designing the present miniature valve 10 relates to the problems associated with forming such a valve with very small lips which are extremely thin and which define a small contact area between the lips. As the thickness of the lips is decreased, problems associated with molded in stresses within the lips increases. Specifically, although the valve may be formed with the lips properly aligned relative to each other prior to the formation of the slit, after the slit has been formed between the lips the molded in stresses may cause the lips to shift and move out of alignment with each other. Thus, it has been found that when a miniature valve on the scale of the present invention is produced, it is preferable to provide a supporting structure which maintains the lips in alignment with each other.

Referring to FIGS. 2-5, and in accordance with the present invention, the duckbill valve 10 is provided with a pair of lips 18, 20 which converge in a direction from an inlet end 22 of the valve toward an outlet end 24 of the valve. The lips 18, 20 each include a respective planar outer wall 26, 28 and a respective planar inner wall 30, 32.

The miniature valve 10 is preferably formed in a molding operation wherein the lips 18, 20 are connected by a lip membrane 34 extending therebetween. In an operation subsequent to the molding operation, the lip membrane 34 is cut in a direction transversely of a longitudinal axis 36 of the valve 10 to form a slit 38 between the lips 18, 20.

It should be noted that a fundamental advantage of duckbill valves over other types of valves is that the duckbill valve is constructed from a single molding and the membrane 34 is then slit with a knife so that a fine structure forming one face for a sealing structure on the membrane 34 will have a mating fine structure forming the opposite sealing face on the membrane 34.

As will be described further below, the lips 18, 20 are formed as very thin flaccid members defining a delicate lip structure in order to obtain the desired operating characteristics for the present miniature valve 10, and a stabilizing structure in the form of a tubular sleeve 40 is therefore provided surrounding the lips 18, 20 and extending to the outlet end 24 in order to stabilize the lips 18, 20 from the ends of the slit 38 and thereby ensure that the opposing fine structures will properly mate and seal.

As may be best seen in FIG. 2, the tubular sleeve 40 includes a first outer wall 42 defining a first diameter for the sleeve 40 and a second outer wall 43 defining a second outer diameter for the sleeve 40 wherein the second diameter of wall 43 is less than the first diameter of wall 42 such that a step is formed at a terminal end 45 of the first outer wall 42.

In addition, a cylindrical inner wall surface 44 of the sleeve 40 extends parallel to the second outer wall surface 43, and the wall surfaces 43 and 44 are connected by an annular end surface 46 which is substantially coplanar with the ends of the lips 18, 20 at the membrane 34. The inner cylindrical surface 44 intersects the outer surfaces 26, 28 of the lips 18, 20 along respective curved intersection lines 48, 50, as is best seen in FIGS. 3 and 4. The areas of the lips immediately adjacent to the lines 48, 50 form a plurality of pivot points defining pivot areas, identified by the areas surrounded by dotted lines 52, 54 in FIG. 2, about which the lips 18, 20 may pivot when they open to permit fluid flow through the valve 10.

It should be noted that the connection between the sleeve 40 and the lips 18, 20 is such that the sleeve 40 forms a coupling with the lips 18, 20 adjacent to the ends of the slit 38 whereby the ends of the lips 18, 20 are held parallel to each other at the membrane 34. In contrast, the curved intersection lines 48, 50 define non-coupled areas between the lips 18, 20 and the sleeve 40 about which the lips 18, 20 may pivot with minimal force transmitted from the sleeve 40 for resisting opening movement of the slit 38. The non-coupled areas are located along the portions of each of the lines 48, 50 closest to the apex thereof and transition areas are defined along the lines 48, 50 between the pivot areas 52, 54 and the coupling areas located adjacent to the ends of the slit. This relationship between the lips 18, 20 and the sleeve 40 is essential in order to ensure that the lips are maintained in their proper operating position as well as to ensure that in spite of the sleeve 40 supporting the lips 18, 20, the slit 38 will open at an extremely low cracking pressure to provide forward flow through the valve 10.

Referring to FIGS. 3 and 5, a flange 56 is provided extending radially outwardly from the outer wall surface 42 of the sleeve 40 adjacent to apex points 59, 61 which lie on the respective curved intersection lines 58, 60 defining the intersection between the lip inner surfaces 30, 32 and a generally cylindrical inner wall portion 63 for the valve 10. The flange 56 provides a mounting surface to locate the miniature valve 10 within a housing, such as the Y-site 12 shown in FIG. 1.

Figure 7:
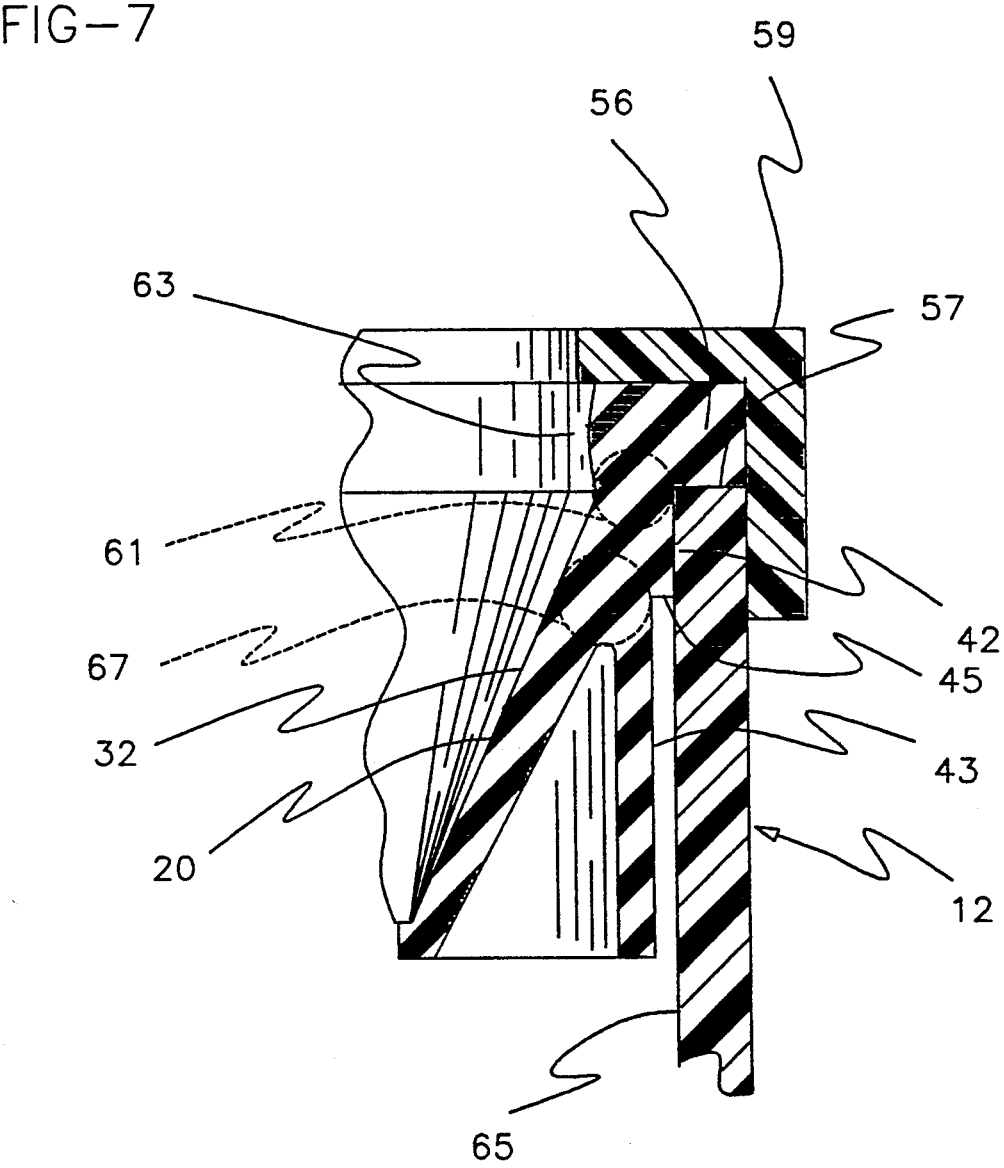
FIG. 7 is a cross-sectional view of one side of the valve shown mounted within a branch of a Y-site.

As is further illustrated in FIG. 7, the flange 56 is typically compressed between a mounting surface 57 and a cap member 59 which may cause a slight inward bulging or flexing of the inner wall 63. It has been found that this flexing of the inner wall 63 in the area of the flange 56, in typical prior art valves, produces a force which is transmitted to the lips 18, 20 and which will tend to bias the slit 38 to an open position. In order to counteract this adverse force, the area between the inner wall 63, at the lip inner walls 30, 32, and the junction between the flange 56 and the first outer wall 42 is designed to be thin to form structurally weak support pivot areas, indicated by dotted line 61, which acts to decouple the lips 18, 20 from forces produced in the area of the flange 56. In addition, thick stable areas 67 are provided immediately adjacent to the support pivot areas 61 and generally defines a material thickness located along a line extending perpendicular to the longitudinal axis 36 from the terminal end 45 of the first outer wall 42 to the respective inner walls 30, 32 of the lips 18, 20 wherein the thickness of the stable areas 67 is greater than the thickness of the support pivot areas 61.

The support pivot areas 61 decouple the lips 18, 20 from pivotal forces produced at the inlet end 22 by the flange 56 by providing a weak connection with the adjacent thick stable areas 67. As a result of this weak connection, the pivoting and compressive forces produced at the first end 22 will be substantially absorbed by the support pivot areas 61 and the flange 56. Thus, it is apparent that it is important for the support pivot areas 61 to be formed as very thin portions of the valve 10.

The first outer wall 42 adjacent to the stable areas 67 ensures that the second outer wall 43 does not contact the inner wall 65 of the site 12 which could result in an undesirable biasing force being applied to the lips 18, 20 from the sleeve 40.

As was noted above, the particular dimensions for the elements forming the miniature valve 10 of the present invention are critical to ensuring that the valve operates within specific predetermined performance 12 parameters. For the present application, the flange 56 has an outer diameter of 0.210 inch, the first outer sleeve wall 42 defines a diameter of 0.164 inch and the second outer sleeve wall 43 defines a diameter of 0.151 inch to form the maximum outer diameters for the valve 10. In addition, the length of the valve from the inlet end 22 to the outlet end 24 is approximately 0.188 inch. These dimensions define the area within which the lips 18, 20 must operate and also dictate certain relationships between various portions of the lips 18, 20 for ensuring that the lips 18, 20 open at the desired cracking pressure as well as provide the desired flow rate, as will be further described below.

Figure 8:
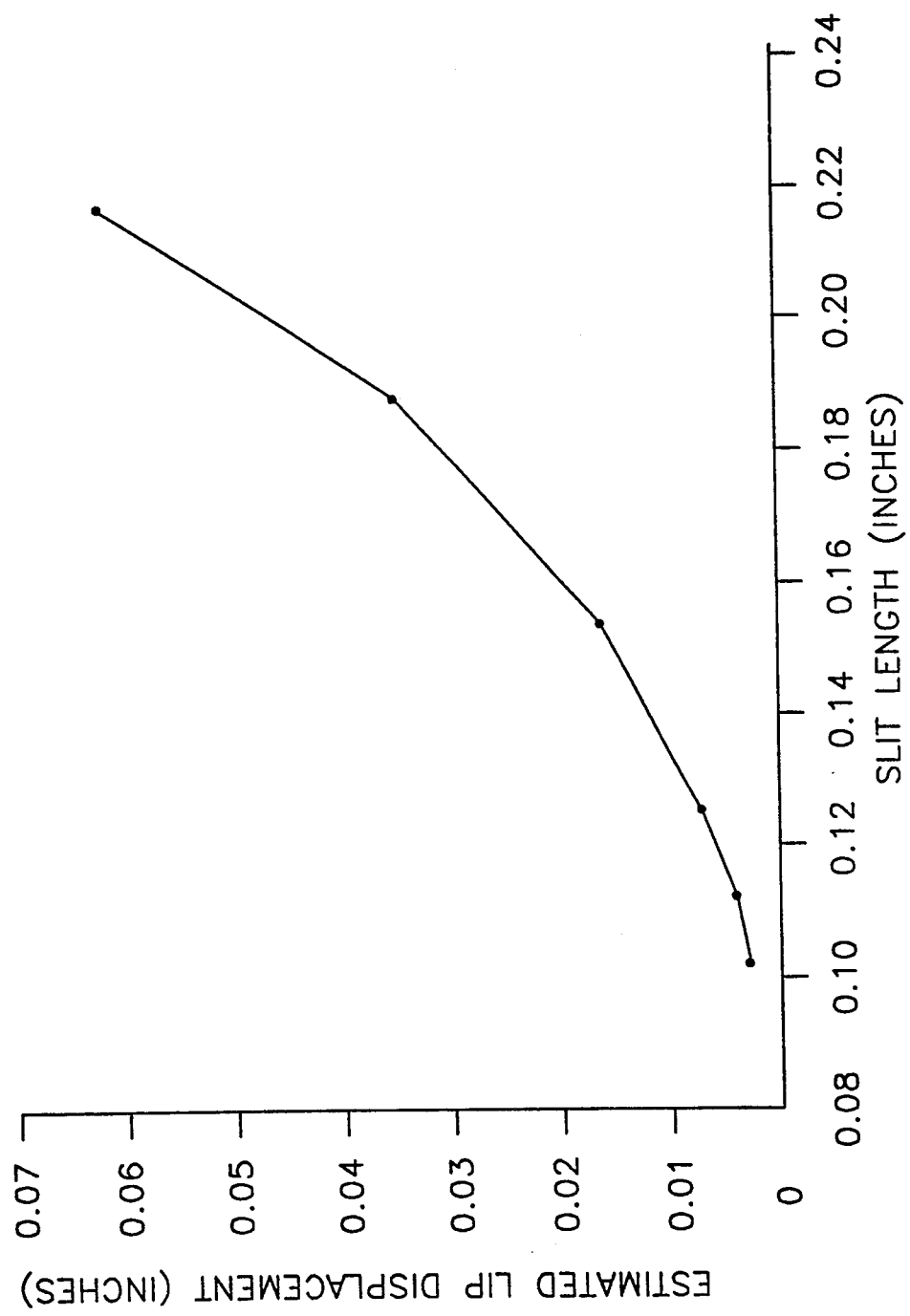
FIG. 8 is a graph plotting the theoretical displacement of the lips in relation to variations in the slit length.

The inner cylindrical wall 44 of the sleeve 40 defines an inner sleeve diameter of approximately 0.125 inch such that the sleeve wall thickness is approximately 0.013 inch. The sleeve wall thickness is minimized in order to accommodate as large a slit length as possible. The slit length for the present valve is preferably equal to the interior diameter of the sleeve wall 44. However, practical limitations imposed by the manufacturing process for the valve prevent bringing the slit length to the full inside diameter of the sleeve 40 such that the length of the slit will be slightly less than the interior diameter of the wall 44. FIG. 8 illustrates that the length of the slit 38 is critical in that small variations in the slit length, which substantially corresponds to the width of the lips 18, 20, can effect large changes in the cracking pressure wherein an increase in the slit length will decrease the cracking pressure.

In addition, the elasticity of the material forming the miniature valve 10 is also important and a medical grade non-toxic silicone is preferable having a one hundred percent Young's modulus of 300 lb/inch$^2$ or less in order to ensure that the lips 18, 20 are sufficiently flexible to both open for fluid flow at a low cracking pressure and to allow a high flow rate to pass through the valve 10. For example, it has been found that by constructing the present valve with a material having a one hundred percent Young's modulus of 235 lb/inch$^2$ and with the small dimensions described herein, a cracking pressure of 2.125 inches of water may be obtained while also providing a volume flow rate in excess of 8,000 ml/hour.

To further provide for high flexibility of the lips 18, 20, the lips 18, 20 are formed as very thin members having a maximum thickness T2 of approximately 0.0198 inch and a minimum thickness T1 of approximately 0.0065 inch, as is shown in FIG. 6. It should be noted that while it is desirable to form the lips as thin as possible, as a practical matter the average lip thickness should be approximately 0.010 inch or greater in order to avoid problems with tearing of the lips, mold-in-stress and non-fills in the mold forming of the valve. Such non-fills may occur in molds for forming high aspect ratio, thin section lips wherein trapped air or poor flow in the mold may cause a non-fill to occur.

The outer walls 26, 28 are connected to the inner cylindrical wall 44 along the intersection lines 48, 50, and a radius of approximately 0.003 inch is defined between each of the walls 26, 28 and the inner cylindrical wall 44 to form a smooth transition therebetween. Further, the distance L from the apex of each of the lines 48, 50 to the second end 24 is approximately 0.090 inch. As was noted above, the connection between the sleeve 40 and the lips 18, 20 is configured such that there is little, if any, coupling or interaction between the inner cylindrical wall 44 and the lips 18, 20 such that the presence of the sleeve 40 does not result in an undesirable increase in the cracking pressure required to initiate fluid flow through the valve 10.

As was also previously noted, the curved lines 48, 50 lie within respective pivot areas 52, 54 for the lips 18, 20, and each of the lips define a pressure area 62, 64 on the respective inner lip surfaces 30, 32. The pressure areas 62, 64 are bounded by the slit 38 and by arcuate lines extending through the pivot areas 52, 54 and following a contour on the inner wall portion which is approximately parallel to the lines 48, 50 and which passes through the pivot areas 52, 54 and transition areas.

In order to produce a miniature valve which operates within the desired parameters, e.g. opening at a pressure of 4 inches of water (at room temperature) or less, it is necessary to maximize the pressure areas 62, 64 to the greatest extent possible, while also reducing the thickness of the lips 18, 20 as much as possible. In order to increase the pressure area 62, 64, the interior diameter of the inner wall portion 63 extending from the inlet end 22 toward the slit 38 and intersecting the lip walls 30, 32 along the lines 58, 60 must be maximized. In the preferred embodiment, the interior diameter D for the inner wall 63 is approximately 0.125 inch such that the pressure areas 62, 64 each define an area of approximately 0.008 inch$^2$.

It should also be noted that as a result of maximizing the diameter D in the interior of the valve 10, the beam length of the lips 18, 20 in the area of the slit 38, measured from edge to edge across each lip 18, 20 in a direction perpendicular to the axis 36, is also maximized and is approximately equal to the diameter D. This results in the lips 18, 20 having greater flexibility to open.

A further factor controlling the cracking pressure at which the lips 18, 20 open is the contact area between the lips 18, 20 at the slit 38. As the contact area is reduced the tendency of the lips to stick closed, which is a somewhat random or unpredictable event, as a result of the natural tackiness of the material forming the valve 10 is also reduced. This contact area is controlled by the thickness of the membrane 34 and in the preferred embodiment, this membrane has a maximum thickness in the direction of the longitudinal axis 36 of approximately 0.006 inch. Again, it should be noted that with the small contact area of the lips 18, 20, the sleeve 40 provides an important function in that it ensures that the lips do not undergo either skewing or echelon movement relative to each other.

It should be understood that skewing, in the present application, refers to a movement of the lips into a non-parallel or angled relationship relative to each other, and echelon movement refers to movement of the end of one lip into overlapping relationship with the opposing lip end, in a longitudinal direction, which may occur while the lips remain substantially parallel to each other. If either a skewing or echelon type misalignment were to occur, the above-described fine mating surfaces would not properly mate together resulting in a poor seal which may permit leakage through the valve.

A miniature valve 10 as constructed according to the above-described characteristics is easily incorporated into existing administration set components without requiring external design changes for the equipment in that only minor internal alternations need to be made in order to provide a mounting location for the present miniature valve 10. In addition, the present valve also operates in accordance with strict performance parameters including providing a cracking pressure at or below 4 inches of water while also providing a high flow rate of 8,000 ml/hour or greater at a pressure of 30 inches of water (at room temperature) applied to the inlet end, which performance parameters have not heretofore been attained to with a miniature valve constructed to the small dimensions of the present valve while also ensuring no back flow leakage.

It should be noted that although flow rates in the range of 8000 ml/hour are not normally used during the administration of fluids to a patient, capacity for such high flow rates is desirable in that the administration set must be purged of air prior to use and the time required for purging is reduced as the flow rate is increased. For example, providing a flow rate of 8000 ml/hour potentially decreases the required purging time by as much as 75 percent as compared to typical prior art valves providing flow rates of 2000 ml/hour.

FIGS. 8-11 illustrate the importance of the particular dimensions of the elements forming the valve structure as the size of the valve becomes very small. These figures provide graphs which are based on theoretical data points computed using a finite element analysis model of the miniature valve of the present invention.

In the graphs shown in FIGS. 8 and 10, the responsiveness of the valve is illustrated in terms of the estimated displacement of each of the lips when a forward fluid pressure of 8 inches of water is applied. In the graphs shown in FIGS. 9 and 11, the responsiveness of the valve is illustrated in terms of the estimated cracking pressure required to initiate forward fluid flow through the valve.

Figure 9:
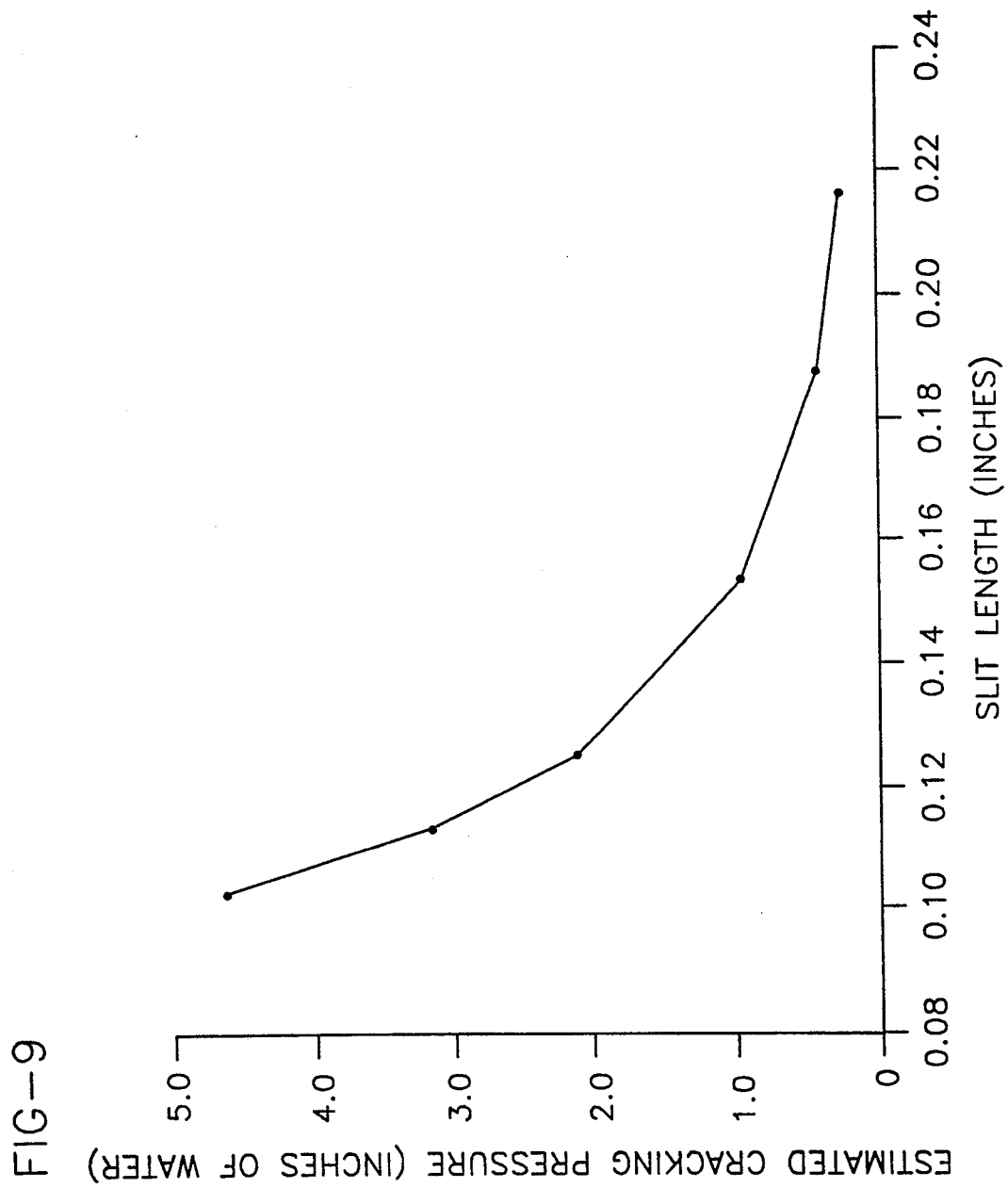
FIG. 9 is a graph plotting the theoretical cracking pressure in relation to variations in the slit length.

As seen in FIGS. 8 and 9, as the slit length decreases, the estimated displacement of the lips, which closely corresponds to fluid flow rate, also decreases and the estimated cracking pressure required to initiate fluid flow increases. The graphs of FIGS. 8 and 9 are computed based on a valve constructed in accordance with the present invention with the exception that the slit length was varied to provide each of the plotted points. It should be noted that as the slit length approaches values of 0.12 and below, only limited displacement of the lips is available, and the cracking pressure also undergoes a steep increase. Thus, it is apparent that the responsiveness of small valves to changes in the slit length is much greater than for valves having dimensions which are only approximately 0.10 inch greater than those of the present valve.

FIGS. 9 and 10 further illustrate the importance of constructing the present valve to particular predetermined dimensions with regard to the thickness of the lips. As seen in these graphs, the estimated displacement of the lips rapidly increases and the estimated cracking pressure rapidly decreases as the thickness of the lips decreases. The graphs of FIGS. 9 and 10 are constructed based on a valve having the same dimensions as the valve of the present invention with the exception that the average lip thickness is changed to provide each of the plotted points. As noted above, the minimum practical average lip thickness due to tearing, molded in stresses and non-fills, is approximately 0.010 inch and, as seen in the graphs, the largest average lip thickness for obtaining an estimated cracking pressure below 4 inches of water is approximately 0.013 inch. Thus, it has been found that the performance of the present miniature valve is very sensitive to changes in the thickness of the lips and that the lips must be constructed having a thickness very close to 0.010 inch in order to provide the desired performance characteristics.

Further, although the lips 18, 20 are formed as highly flexible flaccid structures and may flex somewhat inwardly during back flow conditions, the tubular sleeve 40 ensures that the lips 18, 20 are maintained in their proper operative relationship relative to each other such that the valve exhibits zero leakage in a back flow direction when subjected to a simple static back flow test at a pressure of 8 inches of water. Also, the sleeve 40 acts to prevent the flexible lip structure from collapsing and inverting, such as may occur when a large back pressure is produced during use of a pump in the administration set.

Finally, it should be noted that in addition to forming a supporting structure for the lips 18, 20, the sleeve 40, which in its mounted position is in close proximity with an interior wall 65 of a component 12 for the administration set, acts to fill a portion of the space between the component wall 65 and the lips 18, 20 whereby the amount of air which may be retained adjacent to the outer surfaces 26, 28 of the lips 18, 20 is reduced and in combination with the small size of the valve 10 providing a very small surface area thereby facilitates purging of air from the administration set prior to use.

While the form of apparatus herein described constitutes a preferred embodiment of the invention, it is to be understood that the invention is not limited to this precise form of apparatus, and that changes may be made therein without departing from the scope of the invention which is defined in the appended claims.

What is claimed is:

1. A miniature duckbill valve for permitting fluid flow in a first direction and for preventing fluid flow in a second opposite direction, said valve comprising:
   a pair of substantially planar lips extending in converging relationship in a direction from an inlet end of said valve to an outlet end of said valve,
   means defining a slit between said lips at said outlet end,
   means defining a cylindrical inner wall intersecting said lips along respective intersection lines, said inner wall and said lips defining a longitudinal axis for said valve,
   means defining a pivot area on each of said lips between said outlet end and said intersection lines, a cylindrical sleeve providing a support structure for said lips adjacent to opposing ends of said slit, and wherein said lips are formed as extremely thin highly flexible members defining a delicate flaccid structure such that a minimal force for resisting opening is applied through said lips from said pivot areas to said slit and said lips are readily deformable by low fluid pressure.

2. The miniature valve of claim 1 wherein said sleeve intersects said lips adjacent to said pivot areas to form highly flexible connections between said sleeve and said lips such that minimal force for resisting opening of said slit is transmitted from said sleeve to said lips through said pivot areas.

3. The miniature valve of claim 2 wherein said lips have an average thickness of approximately 0.010 inch whereby said lips form said delicate flaccid structure.

4. The miniature valve of claim 3 wherein the distance, along said longitudinal axis of said valve, from said slit to an apex of said pivot areas is approximately 0.090 inch and said sleeve has a maximum outer diameter of approximately 0.164 inch such that said miniature valve is formed as a very small member.

5. The miniature valve of claim 4 wherein said valve is formed of a medical grade elastomer having a one hundred percent Young's modulus of approximately 300 lb/inch$^2$ or less such that said miniature valve is formed as a highly flexible member.

6. The miniature valve of claim 2 wherein said pivot areas are defined along arcuate lines.

7. The miniature valve of claim 1 wherein said inner wall defines an inner diameter of approximately 0.125 inch and said sleeve defines a maximum outer diameter of approximately 0.164 inch such that said miniature valve is formed as a very small member, and said valve accommodates a relatively high volume flow rate of at least 8000 ml/hour at a pressure of 30 inches of water and has a relatively low forward flow cracking pressure of 4 inches of water or less.

8. The miniature valve of claim 1 wherein a membrane is formed on each of said lips to define narrow contact areas on each of said lips, said contact areas each having a dimension in a direction parallel to said longitudinal axis of approximately 0.006 inch, a said sleeve preventing skewing and echelon movement between said contact areas during opening and closing of said slit.

9. A miniature duckbill valve for permitting fluid flow in a first direction and for preventing fluid flow in a second opposite direction, said valve comprising:

a pair of substantially planar lips extending in converging relationship in a direction from an inlet end of said valve to an outlet end of said valve, means defining a slit between said lips at said outlet end, means defining a cylindrical inner wall intersecting said lips along respective intersection lines, said inner wall and said lips defining a longitudinal axis for said valve, means defining a lip pivot area on each of said lips between said outlet end and said intersection lines, a cylindrical sleeve extending around said lips and supporting said lips adjacent to opposing ends of said slit at said second end of said valve, and wherein said sleeve is formed with first and second outer diameters, said first outer diameter being larger than said second outer diameter for cooperating with a cylindrical interior wall of a housing for mounting said miniature valve such that said second outer diameter is maintained out of contact with the housing.

10. The miniature valve of claim 9 wherein said sleeve intersects said lips adjacent to said lip pivot areas, and a support pivot area is defined between said lip pivot areas and said inlet end of said valve for decoupling said lips from pivotal forces produced at said inlet end.

11. The miniature valve of claim 10 including a flange extending radially outwardly adjacent to said first outer diameter and said first outer diameter has a terminal end adjacent to said second outer diameter located between said flange and said lip pivot areas.

12. The miniature valve of claim 11 wherein said support pivot area is located substantially between said inner wall and a junction between said flange and said first outer diameter of said sleeve wherein the thickness of said support pivot area, measured as the distance between said junction and said inner wall, is less than the thickness of a thick stable area, measured as the distance from said terminal end to an inner surface on one of said lips in a direction perpendicular to said longitudinal axis, such that pivotal forces produced at said inlet end during compression of said flange will be decoupled from said lips in said support pivot area, and said thick stable area will provide a stable support for said lips substantially unaffected by forces applied at said inlet end.

13. The miniature valve of claim 10 wherein said lips have an average thickness of approximately 0.010 inch whereby said lips form a delicate flaccid structure, and highly flexible connections are formed in said lip pivot areas such that minimal force for resisting opening of said slit is transmitted from said sleeve to said lips through said lip pivot areas.

14. The miniature valve of claim 13 wherein said first outer diameter is approximately 0.164 inch and said second outer diameter is approximately 0.151 inch such that said second outer diameter is adapted to be located spaced from and in close proximity to the cylindrical inner wall of the housing to avoid transmission of forces to said lips from the housing via said second outer diameter while also limiting the spacing between said second outer diameter and the housing to minimize the retention of air adjacent to said valve.

15. The miniature valve of claim 9 including a pressure area defined on each of said lips by an interior surface bounded by a respective one of said lip pivot areas and said slit and by transitional areas extending from opposing sides of said lip pivot areas toward said slit wherein each of said pressure areas is approximately 0.008 inch$^2$.

16. The miniature valve of claim 15 wherein said valve has a forward flow cracking pressure of 4 inches of water or less, and said valve accommodates a volume flow rate of at least 8000 ml/hour at a pressure of 30 inches of water.

17. A miniature duckbill valve for permitting fluid flow in a first direction and for preventing fluid flow in a second opposite direction, said valve comprising:

a pair of substantially planar lips extending in converging relationship in a direction from an inlet end of said valve to an outlet end of said valve, means defining a slit between said lips at said outlet end, means defining a cylindrical inner wall intersecting said lips along respective intersection lines, said inner wall and said lips defining a longitudinal axis for said valve, means defining a lip pivot area on each of said lips between said outlet end and said intersection lines, a cylindrical sleeve extending around said lips and supporting said lips adjacent to opposing ends of said slit at said second end of said valve, said sleeve intersecting said lips adjacent to said lip pivot areas to form highly flexible connections between said sleeve and said lips such that minimal force for resisting opening of said slit is transmitted from said sleeve to said lips through said lip pivot areas, said sleeve being formed with a first outer diameter of 0.164 inch and a second outer diameter of 0.151 inch, said first outer diameter being larger than said second outer diameter for cooperating with a cylindrical interior wall of a housing for mounting said miniature valve such that said second outer diameter is maintained out of contact with the housing, and wherein said miniature valve is formed of a medical grade silicone having a one hundred percent Young's modulus of 300 lb/inch$^2$ or less, and said lips are formed as extremely thin highly flexible members having an average thickness of 0.010 inch such that a minimal force for resisting opening is applied through said lips from said lip pivot areas to said slit.

18. The miniature valve of claim 17 including a flange extending radially outwardly adjacent to said first outer diameter, said valve having a maximum length of approximately 0.188 inch such that said miniature valve is formed as a very small member.

19. The miniature valve of claim 18 wherein said first outer diameter has a terminal end adjacent to said second outer diameter and including a support pivot area longitudinally located between said lip pivot areas and said inlet end and substantially situated between said inner wall and a junction between said flange and said first outer diameter of said sleeve, wherein the thickness of said support pivot area, measured as the distance between said junction and said inner wall, is less than the thickness of a thick stable area, measured as the distance from said terminal end to an inner surface on one of said lips in a direction perpendicular to said longitudinal axis, such that pivotal forces produced at said inlet end during compression of said flange will be decoupled from said lips in said support pivot area, and said thick stable area will provide a stable support for said lips substantially unaffected by forces applied at said inlet end.

20. The miniature valve of claim 19 including a pressure area defined on each of said lips by an interior surface bounded by a respective one of said lip pivot areas and said slit and by transitional areas extending from opposing sides of said pivot areas toward said slit wherein each of said pressure areas is approximately 0.008 inch$^2$, said valve having a forward flow cracking pressure of 4 inches of water or less, and said valve accommodating a volume flow rate of at least 8000 ml/hour at a pressure of 30 inches of water.

* * * * *